United States Patent
Mao et al.

(10) Patent No.: US 8,513,415 B2
(45) Date of Patent: Aug. 20, 2013

(54) PREPARATION OF C-PYRAZINE-METHYLAMINES

(75) Inventors: Yunyu Mao, Brooklyn, NY (US); Josef A. Rechka, Port Jefferson, NY (US); Paula A. Tavares-Greco, Farmingdale, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 0 days.

(21) Appl. No.: 13/265,363

(22) PCT Filed: Apr. 19, 2010

(86) PCT No.: PCT/US2010/031547
§ 371 (c)(1),
(2), (4) Date: Oct. 20, 2011

(87) PCT Pub. No.: WO2010/123792
PCT Pub. Date: Oct. 28, 2010

(65) Prior Publication Data
US 2012/0041202 A1   Feb. 16, 2012

Related U.S. Application Data

(60) Provisional application No. 61/170,911, filed on Apr. 20, 2009.

(51) Int. Cl.
*C07D 241/02* (2006.01)

(52) U.S. Cl.
USPC .......................................................... 544/409

(58) Field of Classification Search
USPC .......................................................... 544/409
See application file for complete search history.

(56) References Cited

U.S. PATENT DOCUMENTS

| | | | |
|---|---|---|---|
| 3,840,537 A | 10/1974 | Garside | |
| 5,217,999 A | 6/1993 | Levitzki | |
| 5,302,606 A | 4/1994 | Spada | |
| 5,326,905 A | 7/1994 | Dow | |
| 5,397,787 A | 3/1995 | Buzzetti | |
| 5,556,874 A | 9/1996 | Dobrusin | |
| 6,194,439 B1 | 2/2001 | Dow | |
| 6,265,411 B1 | 7/2001 | Thomas | |
| 6,337,338 B1 | 1/2002 | Kozlowski | |
| 6,362,336 B1 | 3/2002 | Lohmann | |
| 6,486,179 B2 | 11/2002 | Jirousek et al. | |
| 6,713,474 B2 | 3/2004 | Hirst | |
| 6,939,874 B2 | 9/2005 | Harmange | |
| 7,087,602 B2 | 8/2006 | Thomas | |
| 7,087,613 B2 | 8/2006 | Norris | |
| 7,115,617 B2 | 10/2006 | Buchanan | |
| 7,202,243 B2 | 4/2007 | Hendrix | |
| 7,232,911 B2 | 6/2007 | Vangelisti | |
| 7,244,733 B2 | 7/2007 | Hunt | |
| 7,271,262 B2 | 9/2007 | La Greca | |
| 7,326,699 B2 | 2/2008 | Capraro | |
| 7,332,497 B2 | 2/2008 | Hirst | |
| 7,345,038 B2 | 3/2008 | Bright | |
| 7,348,358 B2 | 3/2008 | Larsson | |
| 7,459,554 B2 | 12/2008 | Dong | |
| 7,534,797 B2 | 5/2009 | Arnold | |
| 7,648,987 B2 | 1/2010 | Crew | |
| 7,820,662 B2 | 10/2010 | Arnold | |
| 7,915,256 B2 | 3/2011 | Andrews | |
| 2002/0076408 A1 | 6/2002 | Buchsbaum | |
| 2003/0108545 A1 | 6/2003 | Rockwell | |
| 2003/0114467 A1 | 6/2003 | Shakespeare | |
| 2003/0144252 A1 | 7/2003 | Furr | |
| 2003/0153752 A1 | 8/2003 | Hirst | |
| 2003/0157104 A1 | 8/2003 | Waksal | |
| 2003/0175763 A1 | 9/2003 | Degenhardt | |
| 2004/0014774 A1 | 1/2004 | Myers et al. | |
| 2004/0052785 A1 | 3/2004 | Goodman | |
| 2004/0057950 A1 | 3/2004 | Waksal | |
| 2004/0092546 A1 | 5/2004 | Wei | |
| 2004/0102655 A1 | 5/2004 | Liang et al. | |
| 2004/0106605 A1 | 6/2004 | Carboni | |
| 2004/0180911 A1 | 9/2004 | Capraro | |
| 2004/0209930 A1 | 10/2004 | Carboni | |

(Continued)

FOREIGN PATENT DOCUMENTS

| | | |
|---|---|---|
| EP | 1 422 220 A1 | 5/2004 |
| JP | 05/089352 A | 4/2005 |

(Continued)

OTHER PUBLICATIONS

Johnson, J.I.et al. (2001) British Journal of Cancer 84:1424-1431.
Jones, H.E. et al. (2004) Endocr Relat Cancer 11:793-814.
Khalil, M.Y. et al. (2003) Expert Rev. Anticancer Ther. 3:367-380.
Kim, E.S. et al. (2001) Current Opinion Oncol. 13:506-513.
Knowlden, J. M. (2005) Endocrinology 146(11):4609-4618.
Kopecky, D. J. et al: "Identification and optimization of N <3>, N<6>-diaryl-1H-pyrazolo [3,4-d] pyrimidine-3, 6-diamines as a novel class of ACK1 inhibitors" Bioorganic & Medicinal Chemistry Letters, Pergamon, Elsevier Science, vol. 18, No. 24. Dec. 15, 2008 pp. 6352-6356.

(Continued)

*Primary Examiner* — Yong Chu
*Assistant Examiner* — Valerie Rodriguez-Garcia

(57) ABSTRACT

A process for preparing a compound of formula (I) or a salt thereof: (I) wherein R1 is H or optionally substituted aryl or heteroaryl; comprising reacting 2,3-dichloropyrazine with a suitable diaryl imine followed by hydrolysis.

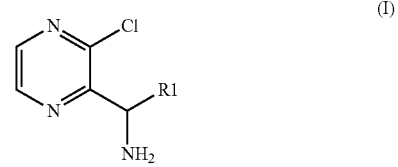

2 Claims, No Drawings

(56) References Cited

U.S. PATENT DOCUMENTS

| | | |
|---|---|---|
| 2004/0220189 A1 | 11/2004 | Sun |
| 2005/0009832 A1 | 1/2005 | Sun |
| 2005/0032759 A1 | 2/2005 | Massimini |
| 2005/0037999 A1 | 2/2005 | La Greca |
| 2005/0054638 A1 | 3/2005 | Barlaam |
| 2005/0136063 A1 | 6/2005 | Wang |
| 2005/0153966 A1 | 7/2005 | Gangloff |
| 2005/0215530 A1 | 9/2005 | Ryan |
| 2005/0215564 A1 | 9/2005 | Stiles |
| 2005/0271747 A1 | 12/2005 | Higgins et al. |
| 2005/0277628 A1* | 12/2005 | Pfau et al. ............ 514/217.03 |
| 2006/0019957 A1 | 1/2006 | Crew |
| 2006/0046977 A1 | 3/2006 | Nunes |
| 2006/0069084 A1 | 3/2006 | Burns |
| 2006/0084654 A1 | 4/2006 | Beck |
| 2006/0154982 A1 | 7/2006 | Larsson |
| 2006/0166992 A1 | 7/2006 | Hendrix |
| 2006/0235031 A1* | 10/2006 | Arnold et al. ............ 514/263.2 |
| 2007/0087613 A1 | 4/2007 | Schumacher |
| 2007/0112005 A1 | 5/2007 | Chen |
| 2007/0149521 A1 | 6/2007 | Crew |
| 2007/0149567 A1 | 6/2007 | Didiuk |
| 2007/0202101 A1 | 8/2007 | Rosen |
| 2007/0203143 A1 | 8/2007 | Sheppard |
| 2007/0238734 A1 | 10/2007 | Nemecek |
| 2007/0254883 A1 | 11/2007 | Crew |
| 2007/0280928 A1 | 12/2007 | Buck |
| 2008/0014200 A1 | 1/2008 | Arnold |
| 2008/0139582 A1 | 6/2008 | Honigberg |
| 2008/0254040 A1 | 10/2008 | Stefanic |
| 2008/0267957 A1 | 10/2008 | Arnold |
| 2009/0093488 A1 | 4/2009 | Buck |
| 2009/0181940 A1 | 7/2009 | Beck |
| 2009/0263397 A1 | 10/2009 | Buck |
| 2009/0286768 A1 | 11/2009 | Crew |
| 2009/0325928 A1 | 12/2009 | Arnold |
| 2010/0286155 A1 | 11/2010 | Buck |
| 2011/0046144 A1 | 2/2011 | Mulvihill |
| 2013/0005733 A1 | 1/2013 | Barr |

FOREIGN PATENT DOCUMENTS

| | | |
|---|---|---|
| WO | 97/28161 A1 | 8/1997 |
| WO | 01/12227 A1 | 2/2001 |
| WO | 01/12604 A1 | 2/2001 |
| WO | 01/72751 A1 | 10/2001 |
| WO | 02/079192 A1 | 10/2002 |
| WO | 03/024967 A2 | 3/2003 |
| WO | 03/080064 A1 | 10/2003 |
| WO | 2006/004703 A2 | 1/2006 |
| WO | 2006/033001 A1 | 3/2006 |
| WO | 2008/106168 A1 | 9/2008 |
| WO | 2009/008992 A2 | 1/2009 |
| WO | 2010/120599 A2 | 10/2010 |
| WO | 2011/163430 A1 | 12/2011 |
| WO | 2012/129145 A1 | 9/2012 |

OTHER PUBLICATIONS

Krishnan, S. et al. (2003) Frontiers in Bioscience 8, e1-13.
Knutsen, L., et al., Journal of the Chemcial Society 1984 vol. 2, pp. 229-238.
Knutsen, L., et al., Journal of the Chemcial Society 1985 pp. 621-630.
Krontiris, T.G., (1994) Internal Medicine 4th Edition, Chapters 71 and 72, pp. 699-729 (Editor is Stein, J.H.).
Kurmasheva, R. T. and Houghton, P. J. (2006) Biochim Biophys Acta 1766:1-22.
Levitzki, A. (2003) Lung Cancer 41 Suppl 1, S9-14.
Li, M. et al. (2002) Clin.Cancer Res. 8:3570-3578.
Liu, B. (2001) Oncogene 20:1913-1922.
Liu, M. et. al. "Synthesis and SAR of 1,9-dihydro-9-hydroxypyraxolo[3,4-b]quinolin-4-ones as novel, selective c-Jun N-terminal kinase inhibitors" Bioorganic & Medicinal Chemistry Letters 2006, 16, 2590-2594.
Lu, D. et al. (2004) J. Biol. Chem. Jan. 23; 279(4): 2856-65.
Lu, Y. et al. (2001) Journal of the National Cancer Institute 93: 1852-1857.
Magne, N. et al. (2002) British Journal of Cancer 86:819-827.
Magne, N. et al. (2003) Clin. Can. Res. 9:4735:4732.
Mahajan, N.P.(2005) Cancer Research 65 (22):10514-10523.
Mahajan, N.P.(2007) PNAS 104 (20): 8438-8443.
Manser, E. et al. (1993) Nature 363 (6427):364-367.
McCarty, M. F. (2004) Integrative Cancer Therapies 3(4): 349-380.
Michelotti, E.L. et. al. "Two classes of p38a MAP kinase inhibitors having a common diphenylether core but exhibiting divergent binding modes" Bioorganic & Medicinal Chemistry Letters 2005, 15, 5274-5279.
Mitchell, W.L. et al. J. Heterocyclic Chem., 1984 vol. 21, No. 3, pp. 697-699.
Miyazaki, Y. et al. "Design and effective synthesis of novel templates, 3,7-diphenyl-4-amino-thieno and furo-[3,2-c] pyridines as protein kinase inhibitors and in vitro evaluation targeting angiogenetic kinases" Bioorganic & Medicinal Chemistry Letters 2007, 17, 250-254.
Morgillo, F. et al. (2006) Cancer Res 66(20):10100-10111.
Mulvihill, M.J. et al: "Novel 2-phenylquinolin-7-yl-derived imidazo[1,5-a]pyrazines as potent insulin-like growth factor-I receptor (IGF-IR) inhibitors" Bioorganic & Medicinal Chemistry, Elsevier Science Ltd. vol. 16, No. 3, Oct. 23, 2007, pp. 1359-1375.
Nahta, R. (2005) Cancer Research 65:11118-111128.
National Library of Medicine—Medical Subject Headings definition of Sarcoma 1999 (http://www.nlm.nih.gov/mesh/2008/MBrowser. html, then type "sarcoma"); last accessed Jul. 1, 2008.
OSI Pharmaceuticals, Inc.:"Study of OSI-906 in Patients with Locally Advanced or Metastatic Adrenocortical Carcinoma", XP-002590463, retrieved from the internet: http://clinicaltrials.gov/show/NCT00924989 (2009).
Pao, W. et al. (2010) Nature Reviews Cancer 10(11) pp. 760-774.
Park, J.O. et al., (2003) Japanese Journal of Clinical Oncology 33 (10) pp. 533-537.
Parrizas, M. et al. (1997) Endocrinology, vol. 138, pp. 1427-1433.
Pink, C.J. et al. (2008) "Organic Solvent Nanofiltration and Absorbents; A Hybrid Approach to Achieve Ultra Low Palladium Contamination of Post Coupling Reaction Products," Organic Process Research & Development, vol. 12, No. 4, pp. 589-595.
Raben, D. et al. (2002) Semin. Oncol. vol. 29, No. 1, suppl 4 (February): pp. 37-46.
Robertson, D. et al., Imidazole-Pyridine Bioisosterism: Comparison of the Intropis Activities of Pyridine- and Imidazole-Substituted 6-Phenyldihydropyridazinone Cardiotonics. J. Med. Chem. 1988, vol. 31, pp. 461-465.
Roskoski, R., Jr. (2004) Biochem Biophys Res Commun 319:1-11.
Smalley Jr., T. L. et al., Synthesis and evaluation of a novel heterocyclic inhibitors of GSK-3. Bioorganic & Medicinal Letters 16 (2006) 2091-2094.
Seymour, L. (2003) Current Opin. Investig. Drugs 4(6):658-666.
Sharma, S.V., et al., 2007 Nature Reviews|Cancer vol. 7, pp. 169-181.
Snow, R.J. et al. "Hit-to-lead studies on benzimidazole inhibitors of ITK: Discovery of a novel class of kinase inhibitors" Bioorganic & Medicinal Chemistry Letters 2007 17 3660-3665.
Solomon, B. et al (2003) Int. J. Radiat. Oncol. Biol. Phys. 55:713-723.
Steinbach, J. P. et al.(2004) Biochem Biophys Res Commun. Aug. 27;321 (3): 524-30.
Thomas, et al. (1998) Expert Opinion Ther. Pat., vol. 8, pp. 475-478.
Thomson, S., et al., 2005 Cancer Res 65 (20) pp. 9455-9462.
Torrance, C.J. et al. (2000) Nature Med. 6:1024-1028.
Tortora, G. et al. (2003) Clin. Cancer Res. 9:1566-1572.
Valeriote, F. et al. (1975) Cancer Chemotherapy Reports (5):895-900.
Van Der Horst, E.T. et al. (2005) PNAS 102 (44):15901-15906.
International Preliminary Report on Patentability and Written Opinion in PCT/US2010/031547 date of issuance of report Oct. 25, 2011.
ISR and WOSA dated Nov. 7, 2011 PCT/US2011/045807.
Database WPI Week 200529, Derwent Publications Ltd., London, GB; (Apr. 7, 2005) AN 2005-277172.
Abushanab, E. and Lee D.Y. Journal of Organic Chemistry, 1975 vol. 40, No. 23, pp. 3376-3378.

Adachi, Y. et al. (2004) CAS Accession #2005:366557, corresponding to Novartis Foundation Symposium 262 (biology of IGF-1), 177-192.
Akio, M. et al. Machine English Translation of JP 07133280, (1995).
Akio, M. et al. (1995) English Language Abstract of JP 07133280.
Albert, A. et al. (1970) Journal of the Chemical Society, vol. 11, pp. 1540-1547.
Albert, A. et al. (1969) Chem. Biol. Pterdines.Proc.Int.Symp., 4th, 4:1-5.
Almeida, M. Q., et al., (2008) J. Clin. Enocrinol Metab 93 (9), pp. 3524-3531.
Arteaga, C.L. and Johnson, D.H. (2001) Current Opinion Oncol. 13:491-498.
Balak, M.N., et al., (2006) Clinical Cancer Res 12(21) pp. 6494-6501.
Baserga, R. (1999) Exp.Cell.Res, vol. 253, pp. 1-6.
Bertino, J. R. et al. (2000), "Part XIV;Oncology, The Principles of Cancer Therapy" Cecil Textbook of Medicine, Goldman, L. et al., 21st Edition, W.B. Saunders Co., Philadelphia, PA, pp. 1060-1070.
Bevacizumab and Gemcitabine Combined with either Cetuximab or Erlotinib in Treating Patients with Advanced Pancreatic Cancer Internet Citation, [Online] Sep. 7, 2004, XP002410261. Retrieved from the Internet: URL: http://www.clinicaltrials.gov/ct/.
Bhattacharya, B.K. et al. Journal of Heterocyclic Chemistry 1993 pp. 1341-1349.
Blair, J. B. et al., Thieno[3,2-b]- and Thieno[2,3-b]pyrrole Bioisoteric Analogues of the Hallucinogen and Serotonin Agonist N,N-Dimethyltryptamine. J. Chem. Med. 1999, 42, 1106-1111.
Breault, G.A., et al., Cyclin-Dependent Kinase 4 Inhibitors as a Treatment for Cancer. Part 2: Identification and Optimisation of Substitiuted 2,4-Bis Anilino Pyrimidines. Bioorganic & Medicinial Chemistry Letters 13 (2003) 2961-2966.
Brown Eric, et al. (2009) Proceedings of the Annual Meeting of the American Association for Cancer Research; 100th Annual Meeting of the American Assoc. for Cancer Research Denver, CA, USA; Apr. 18-22, 2009 vol. 50 p. 419.
Buck, E., et al., (2008) European Journal of Cancer Supplement vol. 6, No. 12, p. 31.
Bulgaru, A.M. et al. (2003) Expert Rev. Anticancer Ther.3:269-279.
Camirand, A. et al. (2005) Breast Cancer Research 2005, 7:R570-R579.
Chakravarti, A. et al.(2002) Cancer Research 62: 200-207.
Ciardiello, F. et al. (2000) Clin. Cancer Res. 6:2053-2063.
Ciardiello, F. et al. (2003) Clin. Cancer Res. 9:1546-1556.
CLINICALTRIALS.gov, US National Institute of Health: "Study of Erlotinib (Tarceva®) in Combination With OSI-906 in Patients With Advanced Non-small Cell Lung Carcinoma (NSCLC) With Activating Mutations of the Epidermal Growth Factor Receptor (EGFR) Gene," OSI Pharmaceuticals XP002677837, retrieved from the Internet: URL:http://clinicaltrials.gov/archive/NCTO 1221077/Feb. 22, 2011.
Contessa, J. N. et al. (1999) Clin. Cancer Res. 5:405-411.
Dancey, J. and Sausville, E.A. (2003) Nature Rev. Drug Discovery 2:296-313.
De Bono, J.S. and Rowinsky, E.K. (2002) Trends in Mol. Medicine 8:S19-S26.
Dineen, et al. "Efficient Transamidation of Primary Carboxamides by in Situ Activation with N, N-Dialkylformamide Dimethyl Acetals" Journal of the American Chemical Society, 2006, 128, 16406-16409.
Dohle, W. et al. "Mild Synthesis of Polyfunctional Benzimidazoles and Indoles by the Reduction of Functionalized Nitroarenes with Phenylmagnesium Chloride" Chemistry a European Journal 2003, 9, 5323-5331.
Dorwald, F.A. Side Reactions in Organic Synthesis, 2005, Wiley: VCH, Weinheim p. IX of Preface p. 1-15, 41, 279-308.
EJC News (2008) European Journal of Cancer vol. 44, No. 2, pp. 167-171.
Expert Opinion Ther. Pat., (1998) vol. 8, pp. 475-478.
Eyzaguirre, A. et al., Proceedings of the Annual Meeting of the American Association for Cancer Research vol. 50 Apr. 1, 2009 pp. 678-679.
Galisteo, M.L. et al. (2006) PNAS 103 (26): 9796-9801.
Goodman and Gilman, (Tenth Edition 2001) Goodman and Gilman's The Pharmacological Basis of Therapeutics Chapter 1, pp. 3-29.
Grunwald, V. and Hidalgo, M. (2003) J. Nat. Cancer Inst. 95:851-867.
Gundisch, D. et al., Synthesis and Evaluation of Pyridazine and Pyrimidine Containing Bioisoteres of (+)-Pyrido[3.4-b]homotropane and Pyrido-[3.4-b]tropane as Novel nAChR Ligands. Bioorganic & Medicinal Chemistry 10 (2002) 1-9.
Guillory J K Ed—Brittan H G: "Generation of Polymorphs, Hydrates, Solvates, and Amorphous Solids," Polymorphism in Pharmaceutical Solids (1999) pp. 183-226, XP002376368 Chapters, I, II and III.
Gupta, R.A. and Dubois, R.N. (2000) Nature Med. 6:974-975.
Gura, et al. (1997) Science 278:1041-1042.
Hartz, R. A. et al. (2002) Bioorganic & Medicinal Chemistry Letters, vol. 12, pp. 291-294.
Heim-Riether, A. et al. Journal of Organic Chemistry, 2005 vol. 70, No. 18, pp. 7331-7337.
Herbst, R.S. et al. (2001) Expert Opin. Biol. Ther. 1:719-732.
Holbro, T. and Hynes, N.E. (2004) Annu Rev Pharmacol Toxicol 44:195-217.
Huang, S. et al. (1999) Cancer Res. 59:1935-1940.
Hurbin, A. et al. (2003) Ann. N.Y. Acad. Sci 1010:354-357.
Ji, Qun-sheng, et al., (2007) Mol Cancer Ther 6 (8) pp. 2158-2167.
Jiang, R. et al. "3,5-Disubstituted quinolines as novel c-Jun N-terminal kinase inhibitors." Bioorganic & Medicinal Chemistry Letters 2007, 17, 6378-6382.
Yang, W. et al. (1999) The Journal of Biological Chemistry 274 (13): 8524-8530.
Yuen, J. SP, et al. (2008) Expert Opinion in Therapeutic Targets 12(5) pp. 589-603.
Zeng, Zhihong et al. (2007) Blood vol. 109, No. 8 pp. 3509-3512.
Ciardiello, F. et al. (2000) Clin. Cancer Res. 6:3739-3747.
Bardel, P., et al. (1994) J. Med. Chem. vol. 37. pp. 4567-4571.

* cited by examiner

PREPARATION OF C-PYRAZINE-METHYLAMINES

This application claims priority of U.S. Appl. No. 61/170,911, filed 20 Apr. 2009, which is incorporated herein by reference in its entirety.

BACKGROUND

The present invention relates to a process for the preparation of C-pyrazine-methylamine compounds, and their conversion to 1,3-substituted-imidazo[1,5-a]pyrazines.

US 2006/0235031 discloses the preparation of C-pyrazine-methylamine compounds, which is different from the process of preparation according to the present invention. The process described in the above-identified application while suitable for the synthesis of small quantities is not ideal for large scale manufacture. Furthermore, the stability of the intermediates from the process in the above-identified publication also needs to be improved. See also U.S. Pat. No. 7,232,911.

There is desire for alternative and improved processes for the preparation of C-pyrazine-methylamine compounds, and their conversion to 1,3-substituted-imidazo[1,5-a]pyrazines with improved scalability, selectivity, efficiency, safety, reduced contamination, and cost.

SUMMARY

The present invention relates to a process for the preparation of C-pyrazine-methylamine compounds. In some aspects, the invention relates to a process for preparing C-pyrazin-2-ylmethylamine compounds of formula (I) or salts thereof:

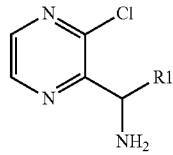

I wherein R1 is H or a substituent such as CN, a carboxylate, or an optionally substituted aryl or a heteroaryl group, by reaction of an appropriate arylimine with a dihalopyrazine, followed by hydrolysis. Another aspect of the invention relates to a process for preparing 1,3-substituted imidazo[1,5-a]pyrazine compounds from a compound of formula I.

DETAILED DESCRIPTION

In some aspects of the invention, there is provided a process for preparing a compound of formula (I) or a salt thereof:

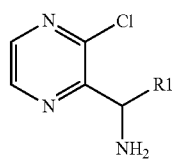

I wherein R1 is H, CN, a carboxylate, or optionally substituted aryl or heteroaryl; comprising reacting a 2,3-dihalopyrazine such as 2,3-dichloropyrazine with a suitable diaryl imine followed by hydrolysis.

In some aspects of the invention, R1 is aryl or heteroaryl, either of which is optionally substituted, such as by aryl, heteroaryl, $C_1$-$C_{10}$alkyl, $C_0$-$C_{10}$alkoxy, halo, or cyano.

In some aspects, the process provides compounds of formula I wherein R1 is aryl or heteroaryl;

In some embodiments, in Step (a) the diaryl imine is prepared by Reaction A:

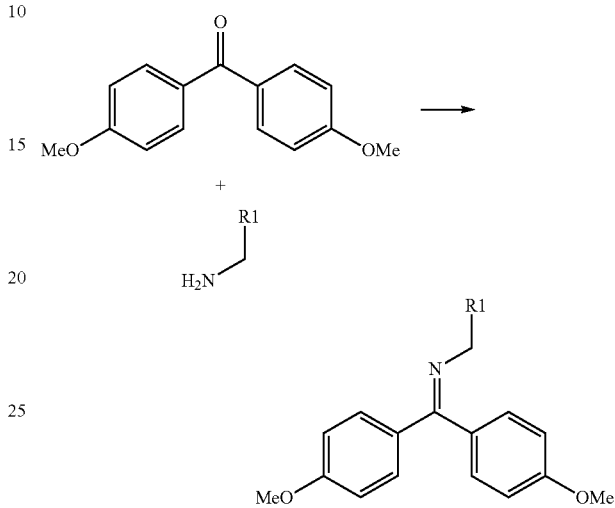

or by Reaction B:

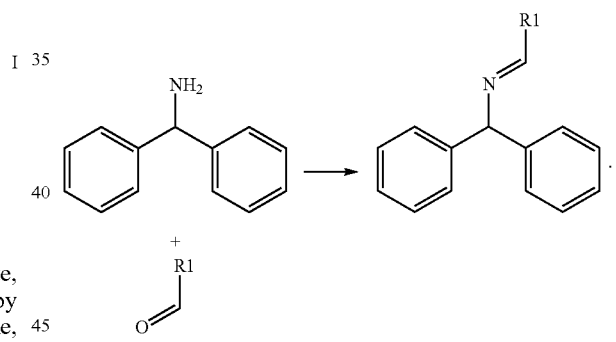

In some embodiments, in Step (b) the diaryl imine product of (a) and the 2,3-dichloropyrazine are reacted together in the presence of base; and in some embodiments in Step (c) the product of (b) is hydrolyzed to obtain the compound of formula I. In some embodiments, Reaction B is used to prepare the diaryl imine.

In some embodiments, R1 is an aryl group selected from phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, or, 2-iodo-4-methylphenyl; and the aryl group is optionally substituted with one or more independent substituents selected from $C_1$-$C_{10}$alkyl, halo, cyano, hydroxy, or phenyl.

In some embodiments, R1 is a heteroaryl group selected from 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, or benzothienyl; and the heteroaryl group is optionally substituted with one or more independent substituents selected from $C_1$-$C_{10}$alkyl, halo, cyano, hydroxy, or phenyl.

In some embodiments, R1 is 2-phenylquinoline.

In some embodiments, at least about 0.5 mol of formula I is obtained in an overall yield for the process of at least about 50%.

In some embodiments, the reaction solvent for (a) comprises THF or 1,4-dioxane.

In some embodiments according to Reaction B of Step (a), a diphenylmethylamine and an aryl aldehyde can be treated in a suitable solvent at a suitable reaction temperature. Suitable solvents include ethers such as THF, glyme, and the like, $CH_3CN$, chlorinated solvents such as $CH_2Cl_2$ or $CHCl_3$, and esters such as EtOAc and the like, and mixtures thereof. Preferred solvents include THF and EtOAc. The reaction can be carried out at about 0° C. to about 120° C., preferably, about 25° C. to about 80° C. The reaction can be carried out at about atmospheric pressure although higher or lower pressures can be used. In some embodiments, approximately equimolar amounts of reactants can be used although higher or lower amounts can be used.

In some embodiments, Reaction A is carried out in the presence of an organic base and a Lewis acid. In some embodiments, the organic base in Reaction A comprises $Et_3N$ or NMM. In some embodiments, the Lewis acid comprises $TiCl_4$. Suitable solvents include ethers such as THF, glyme, and the like, $CH_3CN$; and chlorinated solvents such as $CH_2Cl_2$ or $CHCl_3$ and mixtures thereof. Preferred solvents include THF and 1,4-dioxane. The reaction can be carried out at about −78° C. to about 120° C., preferably, about −78° C. to about 20° C. The reaction can be carried out at about atmospheric pressure although higher or lower pressures can be used. In some embodiments, approximately equimolar amounts of reactants can be used although higher or lower amounts can be used.

In some embodiments, the reaction (b) of the diaryl imine with 2,3-dichloropyrazine is carried out in the presence of a metal hexamethyl disilazide, a metal amide, a metal hydride, a hindered alkoxide such as a tert-butoxide or tert-pentoxide, a metal carbonate or an organic base such as DBU.

In some embodiments of reaction Step (b), 2,3-dichloropyrazine and a (diphenylmethylidene)methanamine compound can be treated with a base in a suitable solvent at a suitable reaction temperature. Suitable solvents for use in the reaction include ethers such as THF, glyme, 1,4-dioxane and the like, and mixtures thereof. Preferred solvents include THF. Suitable bases include HMDS sodium salt or potassium tert-butoxide. The reaction can be carried out at about −78° C. to about 50° C., preferably about −20° C. to about 25° C. The reaction can be carried out at about atmospheric pressure although higher or lower pressures can be used. In some embodiments, approximately equimolar amounts of reactants can be used although higher or lower amounts can be used.

In a typical preparation according to Step (c), a 1-(3-chloropyrazin-2-yl)-N-(diphenylmethylidene)methanamine compound is treated with an acid, in a suitable solvent at a suitable reaction temperature. Suitable acids include HCl, sulfuric acid, or TFA. Suitable solvents for use in the reaction include ethers such as THF, glyme, and the like, esters such as EtOAc and the like, $CH_3CN$, chlorinated solvents such as $CH_2Cl_2$ or $CHCl_3$, toluene, or HCl in MeOH. If desired, mixtures of these solvents can be used. Preferred solvents include $CH_2Cl_2$, EtOAc, THF and toluene. The reaction can be carried out at about −40° C. to about 60° C., preferably, about 0° C. to about 40° C. The reaction can be carried out at about atmospheric pressure although higher or lower pressures can be used. In some embodiments, approximately equimolar amounts of reactants can be used although higher or lower amounts can be used.

In some embodiments, in Step (a) the diaryl imine is prepared by Reaction C:

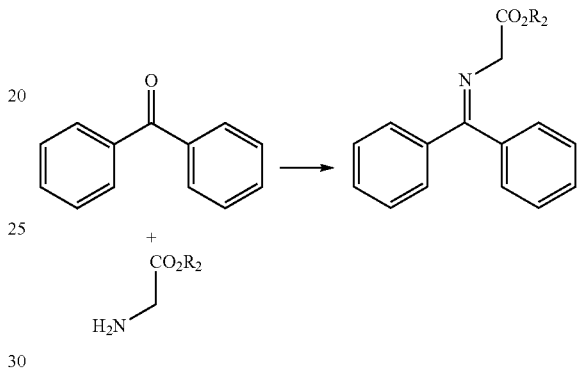

wherein $R_2$ is $C_1$-$C_{10}$alkyl; (b) the diaryl imine product of (a) and the 2,3-dichloropyrazine are reacted together in the presence of base; and (c) the product of (b) is hydrolyzed to obtain the compound of formula I wherein R1 is H.

In some embodiments, $R_2$ is selected from methyl, ethyl, n-propyl, isopropyl, n-butyl, sec-butyl, isobutyl, tert-butyl, n-pentyl, isopentyl, n-hexyl, n-heptyl, isooctyl, nonyl, decyl, any of which can be substituted by one or more independent substituents selected from $C_1$-$C_{10}$alkyl, halo, cyano, hydroxy, or phenyl. In some embodiments, $R_2$ is methyl.

In some embodiments, at least about 0.5 mol of formula I is obtained in an overall yield for the process of at least about 50%.

In some embodiments, Reaction C is carried out in the presence of DIEA or $Et_3N$.

In some embodiments, the base for (b) comprises potassium carbonate or cesium carbonate.

In some embodiments, (c) is carried out in the presence of potassium hydroxide, sodium hydroxide, or lithium hydroxide. In some embodiments, (c) is carried out in the presence of HCl, TFA, acetic acid, or sulfuric acid.

In some embodiments, an advantage of this process is that (3-chloropyrazin-2-yl)methanamine can be made without resorting to the formation of halomethyl pyrazine which is lacrymatory and difficult to form selectively.

In some embodiments of Reaction C, benzophenone can be reacted with a glycine alkyl ester in a suitable solvent at a suitable reaction temperature in the presence of a base. Suitable solvents for use in the reaction included THF, glyme, and the like, propionitrile, acetonitrile, nonpolar solvents such as toluene, and chlorinated solvents such as $CH_2Cl_2$ or $CHCl_3$, or solvent mixtures. A preferred solvent is toluene. The reaction can be carried out at about −20° C. to about 120° C., preferably about 20° C. to about 120° C. Bases such as DIEA or $Et_3N$ can be used. The reaction can be carried out at about atmospheric pressure although higher or lower pressures can be used. In some embodiments, approximately equimolar amounts of reactants can be used although higher or lower amounts can be used.

In some embodiments, the resulting glycine benzophenone imine compound can be reacted with 2,3-dichloropyrazine in a suitable solvent at a suitable temperature. Suitable solvents for use in the above process include THF, glyme, and the like, DMF, DMSO, propionitrile, $Et_3N$, nonpolar solvents such as toluene, and chlorinated solvents such as $CH_2Cl_2$ or $CHCl_3$, or solvent mixtures. A preferred solvent is DMF. The reaction can be carried out at about $-20°$ C. to about $130°$ C., preferably, about $20°$ C. to about $130°$ C. Bases such as potassium carbonate, cesium carbonate, DBU, or other bases can be used. The reaction can be carried out at about atmospheric pressure although higher or lower pressures can be used. In some embodiments, approximately equimolar amounts of reactants can be used although higher or lower amounts can be used.

In some embodiments, the resulting alkyl 2-(3-chloropyrazin-2-yl)-2-(diphenylmethyleneamino)acetate compound can be hydrolyzed in a suitable acid and/or a suitable base at a suitable reaction temperature. Suitable acids for use in the above process include HCl, TFA, acetic acid, and sulfuric acid. A preferred acid is HCl. Suitable bases include potassium hydroxide, sodium hydroxide, and lithium hydroxide. A preferred base is sodium hydroxide. Suitable solvents include water; nonpolar solvents such as toluene, alcohols, ethers such as THF, and chlorinated solvents such as $CH_2Cl_2$ or $CHCl_3$, or solvent mixtures. A preferred solvent is toluene. The reaction can be carried out at about $-20°$ C. to about $80°$ C., preferably, about $20°$ C. to about $50°$ C. The reaction can be carried out at about atmospheric pressure although higher or lower pressures can be used. In some embodiments, approximately equimolar amounts of reactants can be used although higher or lower amounts can be used.

In some embodiments, the process further comprises reacting the compound of formula I according to the reactions:

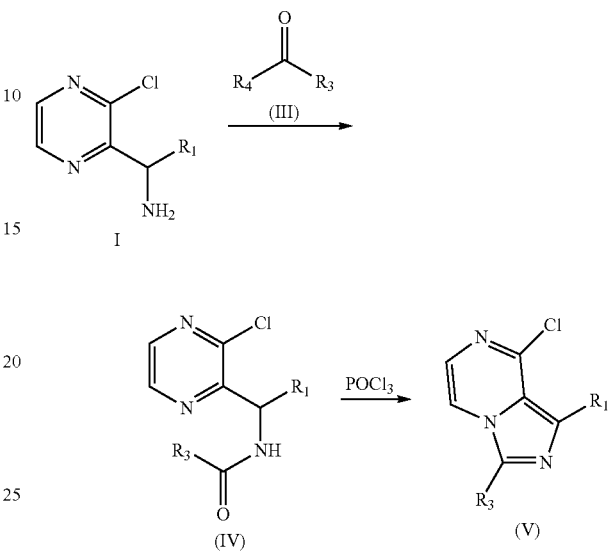

wherein $R_3$ is $C_1$-$C_{10}$alkyl, $C_3$-$C_{12}$cycloalkyl, aryl, or heteroaryl, any of which is optionally substituted by one or more independent substituents selected from halo, oxo, cyano, hydroxy, and $C_1$-$C_{10}$alkyl; and $R_4$ is hydroxy, alkoxy, chloro, or imidazole.

In some embodiments, the process further comprises the reactions:

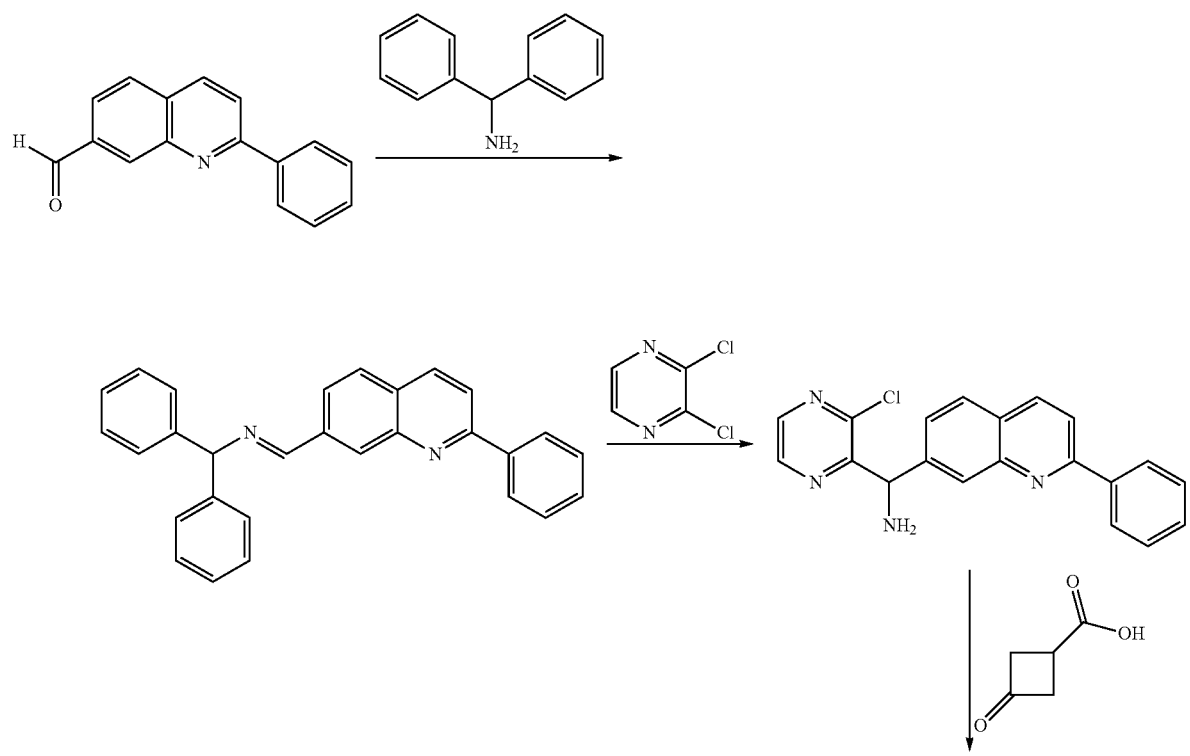

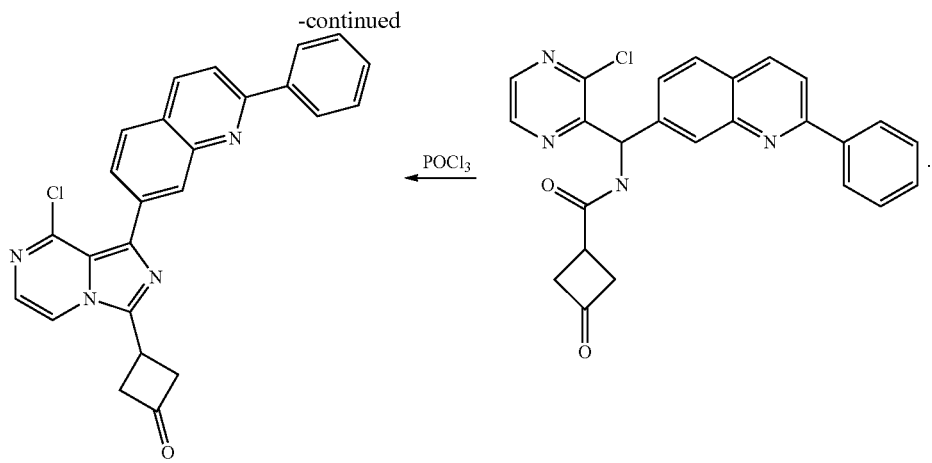

In some embodiments of the preparation of a compound of Formula (IV), a compound of formula (I) and a compound of Formula (III) are reacted under suitable amide coupling conditions. Suitable conditions include treating compounds of Formula (I) and (III) (when $R_4$=OH) with coupling reagents such as DCC or EDC in conjunction with DMAP, HOBt, HOAt and the like. Suitable solvents include ethers such as tetrahydrofuran THF, glyme, and the like, DMF, DMSO, $CH_3CN$, EtOAc, or halogenated solvents such as $CHCl_3$ or $CH_2Cl_2$, and solvent mixtures. Preferred solvents include $CH_2Cl_2$ and DMF. The process can be carried out at about 0° C. to about 80° C., preferably about room temperature (rt). The reaction can be carried out at about atmospheric pressure although higher or lower pressures can be used. In some embodiments, approximately equimolar amounts of reactants can be used although higher or lower amounts can be used.

In some embodiments, compounds of Formula (I) and (III) (where $R_4$=Cl, Br, I) can be reacted with bases such as $Et_3N$ or DIEA or the like optionally in conjunction with DMAP or the like. Suitable solvents include ethers such as THF, glyme, and the like, DMF, $CH_3CN$, EtOAc, halogenated solvents such as $CH_2Cl_2$ or $CHCl_3$, or mixtures thereof. A preferred solvent is $CH_2Cl_2$. The process can be carried out at about −20° C. to about 40° C., preferably about 0° C. to about 25° C. The reaction can be carried out at about atmospheric pressure although higher or lower pressures can be used. In some embodiments, approximately equimolar amounts of reactants can be used although higher or lower amounts can be used. In some embodiments, substantially equimolar amounts of compounds of Formula (I) and (III) (where $R_4$=Cl, Br, I) and base and substoichiometric amounts of DMAP can be used. Other suitable reaction conditions for the conversion of a compound of Formula (I) to a compound of Formula (IV) can be found in Larock, R. C. *Comprehensive Organic Transformations*, $2^{nd}$ ed.; Wiley and Sons: New York, 1999, pp 1941-1949.

In some embodiments of the preparation of a compound of formula (V), an intermediate of Formula (IV) can be treated with $POCl_3$, with or without a suitable solvent at a suitable reaction temperature. Suitable solvents include ethers such as THF, glyme, DMF, EtOAc, and the like, $CH_3CN$, and chlorinated solvents such as $CH_2Cl_2$ or $CHCl_3$, or mixtures of solvents. Preferred solvents include $CH_3CN$; DMF, and $CH_2Cl_2$. The above process can be carried out at about 0° C. to about 120° C., preferably about 20° C. to about 95° C. The reaction can be carried out at about atmospheric pressure although higher or lower pressures can be used. In some embodiments, approximately equimolar amounts of reactants can be used although higher or lower amounts can be used.

All processes of preparation, as described above, are supplemented by synthetic methods known in the art of organic chemistry, or modifications and derivatizations that are familiar to those of ordinary skill in the art. The starting materials used herein are commercially available or may be prepared by routine methods known in the art.

EXAMPLES

Example 1

N-[bis(4-methoxyphenyl)methylidene]-1-(2-phenylquinolin-7-yl)methanamine

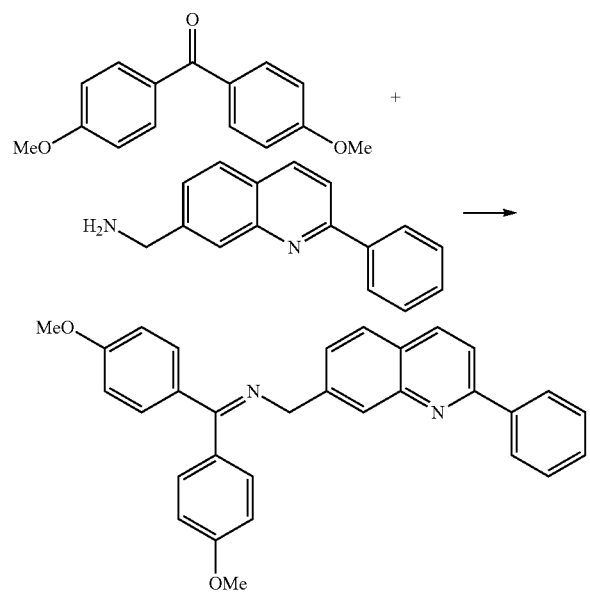

C-(2-Phenylquinolin-7-yl)methylamine (170 mg, 0.73 mmol) and 4,4'-dimethoxybenzophenone (176 mg, 0.73 mmol) were added to a flask under nitrogen. THF (4 mL) and triethylamine (0.30 mL, 2.2 mmol) were then added. The mixture was cooled to −78° C. and titanium tetrachloride (0.080 mL, 0.73 mmol) was added. The reaction mixture was allowed to warm to room temperature. After stirring for 30 minutes the mixture was cooled to −78° C. and triethylamine (2 mL) was added followed by water (3 mL). The mixture was warmed to room temperature and DCM was added. The organic solution was washed with water, dried over sodium sulfate, filtered, and concentrated to dryness in vacuo. The resultant yellow oil was purified by silica gel chromatography (eluted with DCM/heptane 2:1). A light yellow solid (0.247 g, yield 74%) was obtained.

$^1$H NMR (400 MHz, CDCl$_3$) δ ppm 3.83 (s, 3H), 3.87 (s, 3H), 4.83 (s, 2H), 6.83-6.91 (m, 2H), 6.94-7.03 (m, 2H), 7.14-7.22 (m, 2H), 7.40-7.58 (m, 4H), 7.65-7.74 (m, 2H), 7.75-7.87 (m, 2H), 8.07-8.23 (m, 4H). Reference: N. Sotomayor *Tetrahedron*, 1994, 50, 2207

Example 2

C-(3-chloropyrazin-2-yl)-C-(2-phenylquinolin-7-yl)methylamine

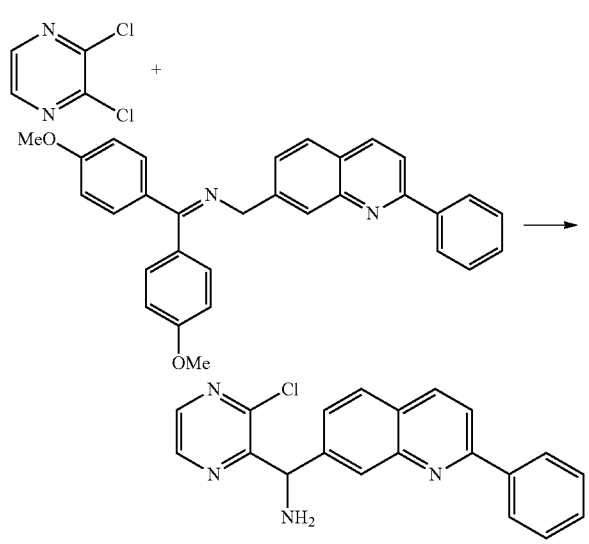

N-[bis(4-methoxyphenyl)methylidene]-1-(2-phenylquinolin-7-yl)methanamine (100 mg, 0.22 mmol) was added to a flask and protected by nitrogen. THF (2 mL) was added and a clear solution was obtained. The solution was cooled to −5° C. and then 1.0 M 1,1,1,3,3,3-hexamethyldisilazane, sodium salt in THF (0.26 mL, 0.26 mol) was added. After 20 min, 2,3-dichloropyrazine (36 mg, 0.24 mmol) in THF (1.0 mL) was added. After a further 20 min, 2M HCl (2 mL) was added and the mixture was stirred at room temperature for 10 min. The aqueous mixture was washed with DCM (3×) and then basified to pH 10 with solid potassium carbonate. A white solid precipitated from the aqueous solution and the resulting suspension was extracted with DCM. The organic solution was washed with water, dried over sodium sulfate, filtered, and concentrated in vacuo to give a light yellow oil (67 mg). The yellow oil was further purified by silica gel chromatography (eluted with ethyl acetate/methanol/triethylamine, 10:0.5:1) to yield a colorless oil (63 mg, 83% yield).

Example 3

1,1-diphenyl-N-((2-phenylquinolin-7-yl)methylene)methanamine

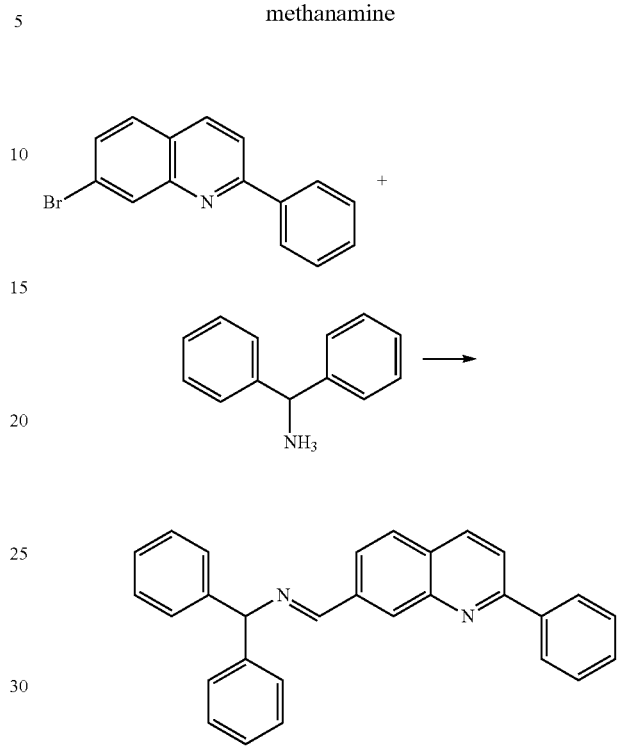

7-Bromo-2-phenyl-quinoline (40.0 g, 0.141 mol) was added to a 1000 mL three-neck round bottom flask (rbf). The flask was degassed and filled with N$_2$. THF (400 mL) was added. The solid dissolved. The flask was kept in a cooling bath (at −62° C.). The off-white solid crashed out at low temperature. 1.4 M of sec-butyllithium in cyclohexane (125.7 mL, 0.176 mol) was added within 15 min, and the internal temperature kept at around −50° C. After addition was complete, the reaction was stirred at −50° C. (internal temperature) for 5 min. DMF (13.6 mL, 0.176 mol) was added within 10 min and the internal temperature was always kept at around −50° C. and the cooling bath was kept at around at −62° C. After 35 min, the reaction was quenched by NH$_4$Cl/water (200 mL), and EtOAc (200 mL) was added. The organic layer was washed with water (300 mL×2) and brine (150 mL), dried over MgSO$_4$, filtered and concentrated in vacuo. After evaporating to almost dryness, EtOAc (200 mL) was added and heated in a 70° C. oil bath to dissolve the solid. Half of the aminodiphenylmethane (26.2 mL, 0.148 mol) was added and the reaction was stirred at 58° C. (internal temperature) for 5 min. The reaction was seeded and the solid came out of solution slowly. After 5 min, the remaining aminodiphenylmethane was added within 3 min. The oil bath temperature was kept at 70° C., the internal temperature increased to 67° C. After 10 min, the reaction mixture was cooled in an ice bath. The off-white solid was collected by vacuum filtration and dried in vacuo at 40-60° C. for 2 hours. The title compound was isolated as an off-white solid (37.42 g, 67% yield).

Example 4

Synthesis of (E)-1,1-diphenyl-N-((2-phenylquinolin-7-yl)methylene)methanamine Via a Different Starting Material from that of Example 3

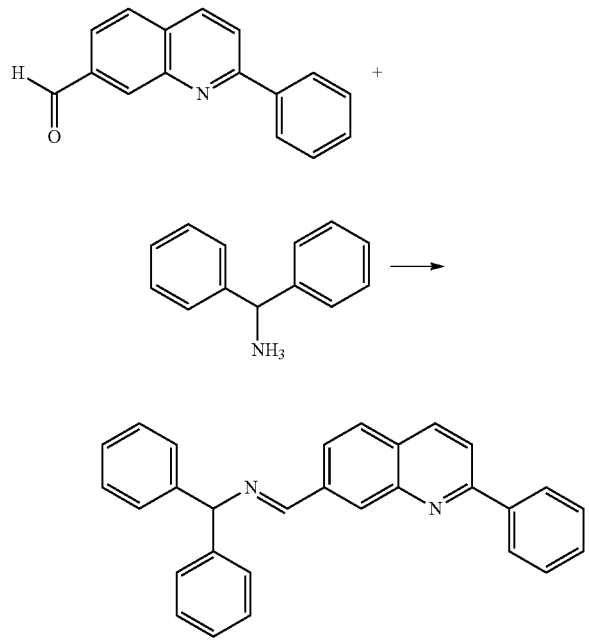

2-Phenylquinoline-7-carbaldehyde (85.00 g, 0.364 mol) and EtOAc (255 mL) were added to a rbf and heated in a 70° C. oil bath. Half of aminodiphenylmethane (70.11 g, 0.38261 mol) was added quickly. After 2 min, a light brown solid precipitated. The reaction was exothermic and the reaction temperature increased to 73° C. The remaining aminodiphenylmethane was then added within 3 min. The reaction temperature decreased to 67° C. slowly. After 30 min, heating was discontinued and the reaction was cooled in an ice bath to about 15° C. The yellow solid was collected by vacuum filtration and dried in vacuo at 45° C. overnight. The title compound was isolated as a yellow solid (115.77 g, 80% yield). $^1$H NMR (400 MHz, CDCl$_3$) δ ppm 5.69 (s, 1H), 7.21-7.28 (m, 2H), 7.31-7.38 (m, 4H), 7.43-7.50 (m, 5H), 7.50-7.57 (m, 2H), 7.84 (d, J=8.59 Hz, 1H), 7.90 (d, J=8.59 Hz, 1H), 8.13-8.19 (m, 2H), 8.22 (d, J=8.08 Hz, 1H), 8.26 (dd, J=8.46, 1.64 Hz, 1H), 8.37 (s, 1H), 8.65 (s, 1H).

Example 5

Synthesis of (3-chloropyrazin-2-yl)(2-phenylquinolin-7-yl)methanamine

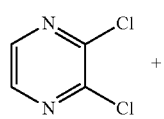

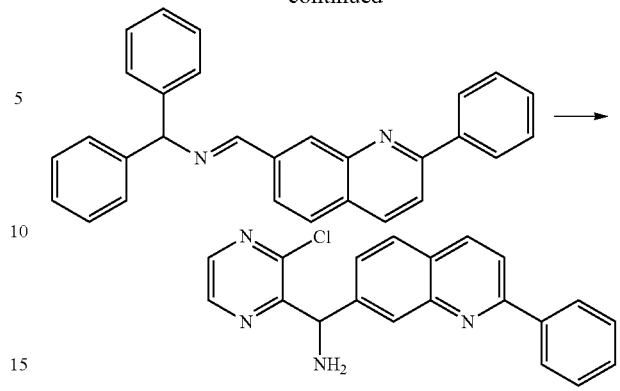

Benzhydryl-[1-(2-phenyl-quinolin-7-yl)-meth-(E)-ylidene]-amine (12.50 g, 31.4 mmol) was added to a 500 mL rbf fitted with a thermocouple. The flask was degassed and filled with nitrogen. THF (150 mL) was added and the solid dissolved. The mixture was cooled to −5° C. and 1.0 M of HMDS sodium salt in THF (39.2 mL) was added within 5 min. The temperature increased slightly to −3° C. The blue solution was stirred for 20 min at 0° C. and then 2,3-dichloropyrazine (5.61 g, 37.6 mmol) in THF (10 ml) was added within 3 min. The mixture was stirred for 30 min and then quenched with saturated NH$_4$Cl/water (200 mL). EtOAc (200 mL) was added and the aqueous phase was removed. Toluene can also be used. The organic layer was washed with water (200 mL×2) and brine (200 mL). Concentrated HCl (10 mL) and water (200 mL) were added. The phases were separated and the organic layer was extracted with 0.1 M HCl (30 mL). The aqueous was washed with EtOAc (2×) and then saturated K$_2$CO$_3$ was used to adjust to pH 10. The aqueous solution was extracted with EtOAc (2×) and the combined organics were dried over Na$_2$SO$_4$, filtered, and concentrated in vacuo to a brown oil which solidified upon standing to yield the title compound as a brown solid (9.94 g, 81% yield). $^1$H NMR (400 MHz, CDCl$_3$) δ ppm 2.30 (br s, 2H), 5.79 (s, 1H), 7.43-7.56 (m, 3H), 7.62 (dd, J=8.46, 1.89 Hz, 1H), 7.81 (d, J=8.34 Hz, 1H), 7.86 (d, J=8.59 Hz, 1H), 8.07 (d, J=1.01 Hz, 1H), 8.10-8.16 (m, 2H), 8.19 (d, J=8.59 Hz, 1H), 8.31 (d, J=2.27 Hz, 1H), 8.60 (d, J=2.53 Hz, 1H). MS (ES+): m/z=347.01/349.03 (100/68) [MH$^+$].

Example 6

Synthesis of HCl salt of (3-chloropyrazin-2-yl)-methylamine

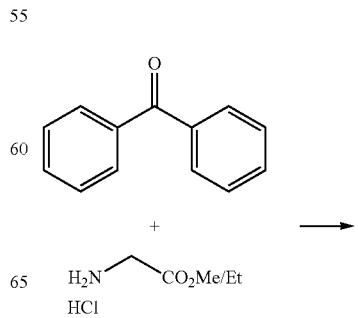

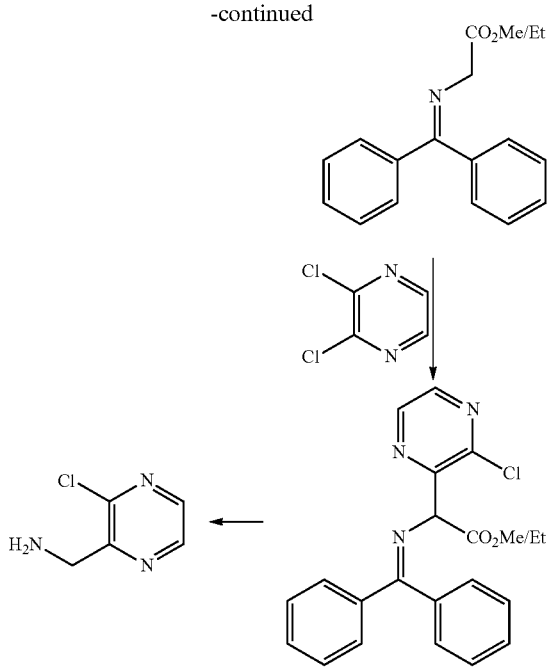

A 500 mL, 1-necked rbf equipped with a magnetic stirrer, and a Dean-Stark apparatus with a nitrogen inlet was charged with benzophenone (58.0 g, 0.318 mol), glycine methyl ester hydrochloride (20 g, 0.159 mol) and toluene (100 mL). The resulting white suspension was heated to reflux and DIEA (56 mL, 0.318 mol) was added over three hours using a syringe pump. The resulting pale yellow solution was stirred at reflux for an additional 1 h. Upon reaction completion, the reaction mixture was cooled to rt. The reaction mixture was then washed with water (50 mL). The layers were separated and the organic solution was washed with water (50 mL) and concentrated in vacuo at 35-40° C. to give (Benzhydrylideneamino)-acetic acid methyl ester (82.59 g). In a similar fashion, (benzhydrylideneamino)-acetic acid ethyl ester was prepared.

A 100 mL rbf equipped with a magnetic stirrer, and a nitrogen inlet was charged with benzhydrylidene-amino)-acetic acid ethyl ester (10 g, 36.6 mmol), $Cs_2CO_3$ (13.27 g, 40.3 mmol) and DMF (50 mL). To the suspension, 2,3-dichloropyrazine (6.13 g, 40.3 mmol) was added. The resulting pale yellow mixture was stirred and heated to 120-125° C. Alternatively, the reaction can be carried out at about 40-60° C. or about 50° C. The resulting dark solution was stirred for 3 h. Upon reaction completion, the reaction mixture was cooled to it, diluted with toluene (50 mL), and washed with water (50 mL). The layers were separated and the bottom aqueous layer was extracted with toluene (2×30 mL). The combined organic layers were washed with water (2×50 mL). The organic layer was concentrated in vacuo at 35-40° C. to remove part of the toluene. This crude material was be hydrolyzed as follows. Alternatively, the method of Example 7 below can be used.

The resultant crude intermediate in toluene was transferred into a 250 mL round bottomed flask equipped with a magnetic stirrer and a nitrogen inlet. Concentrated HCl (37%, 4.0 g, 40.3 mmol) was added and the reaction was allowed to stir at rt for 3 h. After the completion of the imine hydrolysis, the reaction mixture was diluted with toluene and the layers were separated. The bottom aqueous layer was washed with toluene (2×20 mL).

The resultant aqueous solution was then transferred into a 250 mL round bottomed flask equipped with a magnetic stirrer and a nitrogen inlet. The solution was cooled to 5-10° C. using an ice/water bath and sodium hydroxide (10 N, 7.8 mL, 76.9 mmol) was added and allowed to stir at rt for 1 h. After the completion of the ester hydrolysis, the reaction mixture was cooled to 5-10° C.

Concentrated HCl (37%, 4.0 g, 40.3 mmol, 2.1 eq) was added and the reaction was allowed to stir at rt for 12 h and then at 40-45° C. for 24 hours. After the completion of the decarboxylation, the reaction mixture was assayed by HPLC. Based on the HPLC assay, the yield was 58%. A sample was evaporated in vacuo to yield a brown solid. $^1$H NMR (400 MHz, DMSO-$d_6$/$D_2O$) δ ppm 4.33 (s, 2H), 8.52 (s, 1H), 8.68 (s, 1H). MS (ES+): m/z=143.98/146.02 (100/80) [MH$^+$].

Example 7

In an alternative approach for hydrolysis, a 72 L round bottom flask equipped with mechanical stirrer, $N_2$ inlet/outlet and thermometer was charged with solution of crude pyrazine imine compound such as produced in Example 6 above (~30 L, 29.9 mol) in toluene. Water (12 L,) and concentrated HCl (3.2 L, 32.9 mol) was added and the reaction mixture was stirred at ambient temperature for 3 h (monitored by TLC). The layers were separated and aqueous layer was extracted with toluene (15 L).

The aqueous solution was charged to the same reactor and concentrated HCl (3.2 L, 32.9 mol) was added. The reaction was heated at 60° C. and monitored by TLC. After completion of the reaction (24-30 h) the reaction mixture was cooled to 5 to 10° C. and the pH was adjusted to 10 with 50% aqueous NaOH (7 L) while maintaining the temperature below 10° C.

To the basic mixture (10 to 15° C.), $Boc_2O$ (7.2 Kg, 32.9 mol) was added and the reaction mixture was warmed to ambient temperature and stirred for 4 h (monitored by TLC). To the batch MTBE (24 L) was added, stirred for 20 min and the organic layer was separated. The aqueous layer was extracted with MTBE (2×12 L). The combined organic phases were concentrated under reduced pressure to remove approximately half of MTBE and the resulting organic solution was transferred to a 50 L jacketed reactor equipped with mechanical stirrer, $N_2$ inlet/outlet and thermometer. The mixture was cooled to between 5 and 10° C. and 20% HCl in 1,4-dioxane (20 L, 109.6 mol) was added slowly while maintaining the internal temperature below 10° C. The reaction mixture was warmed to ambient temperature and stirred for 4 h. The solids were filtered and washed with MTBE (10 L) and dried in vacuum oven at 40° C. for 6 h to afford the desired compound as a dark brown solid. $^1$H NMR (400 MHz, DMSO-$d_6$): δ 8.82 (br s, 3H), 8.72 (d, J=2.5 Hz, 1H), 8.54 (d, J=2.3 Hz, 1H), 4.22 (s, 2H).

$^1$H NMR (400 MHz or 300 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. Flash chromatography was performed with silica gel (400-230 mesh). Mass-directed HPLC purification of compounds was performed on a Waters system composed of the following: 2767 Sample Manager, 2525 Binary Gradient Module, 600 Controller, 2487 Dual λ Absorbance Detector, Micromass ZQ2000 for ionization, Phenomenex Luna 5μ C18(2) 100 Å 150×21.2 mm 5μ column with mobile phases of 0.01% formic acid acetonitrile (A) and 0.01% formic acid in HPLC water (B), a flow rate of 20 mL/min, and a run time of 13 min. LC-MS data was collected on ZQ2, ZQ3, or HPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ particle size, 4.6×50 mm with a mobile phase of acetonitrile (A) and 0.01% formic acid in HPLC water (B). All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters UPLC-ACQUITY system consists of an ACQUITY sample manager attached to ACQUITY SQ MS and ACQUITY PDA detectors. It uses an ACQUITY UPLC BEH® C18 2.1×50 mm 1.7 μm column with a mobile phase of 0.1% formic acid in water (A) and 0.1% formic acid in acetonitrile (B). UV detection is at 254 nm, and the MS utilizes electrospray ionization in positive mode (ES+). All melting points were determined with a MeI-Temp II apparatus and are uncorrected. Elemental analyses were obtained by Atlantic Microlab, Inc., Norcross, Ga.

DEFINITIONS AND ABBREVIATIONS

As used herein, the term "aryl" refers to an all-carbon monocyclic, bicyclic, or polycyclic groups of 6 to 12 carbon atoms having a completely conjugated pi-electron system. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl) phenyl, and 2-iodo-4-methylphenyl.

The terms "heteroaryl" refer to a monocyclic, bicyclic, or polycyclic group of 5 to 12 ring atoms containing one or more ring heteroatoms selected from N, O, and S, the remaining ring atoms being C, and, in addition, having a completely conjugated pi-electron system. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

The term "alkyl" means both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, and the like.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "halo" refers to fluoro, chloro, bromo, or iodo.

Unless otherwise specified, the term "cycloalkyl" refers to a carbon mono-cyclic, bicyclic, or polycyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

TABLE 1

| | Abbreviations |
|---|---|
| Bn | Benzyl group |
| Boc | tert-butoxycarbonyl |
| BOP | Bis(2-oxo-3-oxazolidinyl)phosphinic |
| Cbz | Benzyloxycarbonyl |
| $CD_3OD$ | Deuterated methanol |
| $CDCl_3$ | Deuterated chloroform |
| CDI | 1,1'-carbonyldiimidazole |
| $CH_2Cl_2$ or DCM | Methylene chloride |
| $CHCl_3$ | Chloroform |
| $CH_3CN$ | Acetonitrile |
| DBN | 1,5-diazabicyclo[4.3.0]non-5-ene |
| DBU | 1,8-diazabicyclo[5.4.0]undec-7-ene |
| DCC | 1,3-dicyclohexylcarbodiimide |
| DEA | Diethylamine |
| DEPC | Diethyl cyanophosphonate |
| DIEA | Diisopropylethylamine |
| DMAP | Dimethylaminopyridine |
| DMC | 2-chloro-1,3-dimethylimidazolinium chloride |
| DMF | N,N-dimethylformamide |
| DMSO | Dimethyl sulfoxide |
| EDC | 1-(3-dimethylaminopropyl)-3-ethylcarbodiimide hydrochloride |
| EDTA | Ethylenediaminetetraacetic acid |
| EGTA | Ethyleneglycol-bis(β-aminoethyl)-N,N,N',N'-tetraacetic Acid |
| ESI | Electrospray Ionization for mass spectrometry |
| $Et_3N$ | Triethylamine |
| EtOAc | Ethyl acetate |
| EtOH | Ethanol |
| Fmoc | Fluorene methyloxycarbonyl |
| HATU | O-(7-azabenzotriazol-1-yl)-N,N,N',N'-tetramethyluronium hexafluorophosphate |
| HBTU | O-benzotriazol-1-yl-N,N,N',N'-tetramethyluronium hexafluorophosphate |
| HCl | Hydrochloric acid |
| HEPES | 4-(2-hydroxyethyl)-1-Piperazineethane sulfonic acid |
| HMDS | 1,1,1,3,3,3-hexamethyldisilazane |
| HOAt | 1-hydroxy-7-azabenzotriazole |
| HOBt | 1-hydroxybenzotriazole hydrate |
| HRMS | High Resolution Mass Spectroscopy (electrospray ionization positive scan) |
| $K_3PO_4$ | Potassium phosphate |
| LCMS | Liquid Chromatography - Mass Spectroscopy |
| LRMS | Low Resolution Mass Spectroscopy |
| MeOH | methanol |
| NaH | Sodium hydride |
| NMM | N-methylmorpholine |
| NMP | 1-methyl-2-pyrrolidinone |
| NMR | Nuclear Magnetic Resonance |
| PG | Protecting group |
| TFA | Trifluoroacetic acid |
| THF | Tetrahydrofuran |
| $TiCl_4$ | Titanium tetrachloride |
| TLC | Thin layer chromatography |

The invention claimed is:
1. A compound of the formula I:
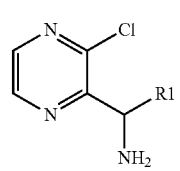
wherein R1 is a carboxylate.
2. The compound of claim 1, wherein R1 is —C(O)OCH$_3$ or —C(O)OCH$_2$CH$_3$.
* * * * *